US011065436B2

(12) United States Patent
Harjes et al.

(10) Patent No.: US 11,065,436 B2
(45) Date of Patent: *Jul. 20, 2021

(54) COMMUNICATION METHODS AND ARCHITECTURE FOR HEART TREATMENT SYSTEMS

(71) Applicant: TC1 LLC, St. Paul, MN (US)

(72) Inventors: Daniel I. Harjes, Acton, MA (US); John Freddy Hansen, Pleasanton, CA (US); Joseph C. Stark, III, San Leandro, CA (US); Ghazal Anvar Mauro, San Ramon, CA (US); Eric Lee, Oakland, CA (US); Justin A. Callaway, Goffstown, NH (US); Onur Dur, Milpitas, CA (US)

(73) Assignee: TC1 LLC, Saint Paul, MN (US)

( * ) Notice: Subject to any disclaimer, the term of this patent is extended or adjusted under 35 U.S.C. 154(b) by 403 days.

This patent is subject to a terminal disclaimer.

(21) Appl. No.: 15/938,883

(22) Filed: Mar. 28, 2018

(65) Prior Publication Data
US 2018/0280599 A1    Oct. 4, 2018

Related U.S. Application Data

(60) Provisional application No. 62/478,452, filed on Mar. 29, 2017.

(51) Int. Cl.
*A61N 1/362* (2006.01)
*A61M 60/50* (2021.01)
(Continued)

(52) U.S. Cl.
CPC ........... *A61M 60/50* (2021.01); *A61B 5/0031* (2013.01); *A61B 5/02405* (2013.01);
(Continued)

(58) Field of Classification Search
CPC .................................................. A61N 1/3629
See application file for complete search history.

(56) References Cited

U.S. PATENT DOCUMENTS 3,911,897 A    10/1975 Leachman
5,139,517 A     8/1992 Corral
(Continued)

FOREIGN PATENT DOCUMENTS

EP    2570143 A1    3/2013
EP    3 213 781 A1  9/2017
(Continued)

OTHER PUBLICATIONS

Bedi et al., "Ventricular Arrhythmias During Left Ventricular Assist Device Support", Am J Cardiol., vol. 99, Issue 8, 2007, pp. 1151-1153.
(Continued)

*Primary Examiner* — Joseph M Dietrich
(74) *Attorney, Agent, or Firm* — Kilpatrick Townsend & Stockton LLP

(57) ABSTRACT

The present invention generally relates to heart treatment systems. In some aspects, methods and systems are provided for facilitating communication between implanted devices. For example, an implantable cardiac rhythm management device may be configured to communicate with an implantable blood pump. The implantable cardiac rhythm management device may deliver heart stimulation rate information in addition to information associated with any detected abnormalities in heart function. In response, the pump may be configured to adjust pumping by the pump to better accommodate a patient's particular needs.

28 Claims, 4 Drawing Sheets

(51) Int. Cl.
*A61B 5/024* (2006.01)
*A61B 5/00* (2006.01)
*A61N 1/372* (2006.01)
*A61M 60/148* (2021.01)
*A61M 60/562* (2021.01)
*A61M 60/113* (2021.01)
*A61M 60/871* (2021.01)

(52) U.S. Cl.
CPC ........ *A61M 60/148* (2021.01); *A61M 60/562* (2021.01); *A61N 1/3629* (2017.08); *A61N 1/37288* (2013.01); *A61M 60/113* (2021.01); *A61M 60/871* (2021.01); *A61M 2205/3334* (2013.01); *A61M 2205/3507* (2013.01); *A61M 2210/125* (2013.01)

(56) References Cited

U.S. PATENT DOCUMENTS

| | | |
|---|---|---|
| 5,318,592 A | 6/1994 | Schaldach |
| 5,503,615 A | 4/1996 | Goldstein |
| 6,066,086 A | 5/2000 | Antaki et al. |
| 6,111,520 A | 8/2000 | Allen et al. |
| 6,278,379 B1 | 8/2001 | Allen et al. |
| 6,585,635 B1 | 7/2003 | Aldrich |
| 6,634,224 B1 | 10/2003 | Schoeb et al. |
| 6,643,420 B2 | 11/2003 | Han et al. |
| 6,772,011 B2 | 8/2004 | Dolgin et al. |
| 6,855,115 B2 | 2/2005 | Fonseca et al. |
| 6,984,201 B2 | 1/2006 | Khaghani et al. |
| 7,029,433 B2 | 4/2006 | Chang |
| 7,245,117 B1 | 7/2007 | Joy et al. |
| 7,320,706 B2 | 1/2008 | Al-Najjar |
| 7,439,723 B2 | 10/2008 | Allen et al. |
| 7,498,799 B2 | 3/2009 | Allen et al. |
| 7,520,850 B2 | 4/2009 | Brockway |
| 7,550,978 B2 | 6/2009 | Joy et al. |
| 7,679,355 B2 | 3/2010 | Allen et al. |
| 7,839,153 B2 | 11/2010 | Joy et al. |
| 7,853,325 B2 | 12/2010 | Dabney et al. |
| 7,862,501 B2 | 1/2011 | Woodard |
| 7,945,333 B2 | 5/2011 | Jacobson |
| 7,963,905 B2 | 6/2011 | Salmonsen et al. |
| 7,988,728 B2 | 8/2011 | Ayre |
| 7,998,054 B2 | 8/2011 | Bolling |
| 8,145,324 B1 | 3/2012 | Stevenson et al. |
| 8,177,838 B2 | 5/2012 | Vodermayer et al. |
| 8,180,448 B2 | 5/2012 | Stevenson et al. |
| 8,224,462 B2 | 7/2012 | Westlund et al. |
| 8,246,530 B2 | 8/2012 | Sullivan |
| 8,295,939 B2 | 10/2012 | Jacobson |
| 8,364,283 B2 | 1/2013 | Halperin et al. |
| 8,506,471 B2 | 8/2013 | Bourque |
| 8,543,205 B2 | 9/2013 | Ostroff |
| 8,608,636 B2 | 12/2013 | Choi et al. |
| 8,657,733 B2 | 2/2014 | Ayre et al. |
| 8,682,431 B2 | 3/2014 | Callaway et al. |
| 8,712,544 B2 | 4/2014 | Dabney et al. |
| 8,771,165 B2 | 7/2014 | Choi et al. |
| 8,794,989 B2 | 8/2014 | Kearsley et al. |
| 8,852,099 B2 | 10/2014 | Von Arx et al. |
| 8,864,644 B2 | 10/2014 | Yomtov |
| 8,894,561 B2 | 11/2014 | Callaway et al. |
| 8,897,887 B2 | 11/2014 | Halperin et al. |
| 9,039,595 B2 | 5/2015 | Ayre et al. |
| 9,090,271 B2 | 7/2015 | Bartonek |
| 9,387,284 B2 | 7/2016 | Heilman et al. |
| 9,433,714 B2 | 9/2016 | Voskoboynikov et al. |
| 9,579,432 B2 | 2/2017 | Tamez et al. |
| 9,579,435 B2 | 2/2017 | Yomtov |
| 9,592,327 B2 | 3/2017 | Wariar et al. |
| 9,833,552 B2 | 12/2017 | Yomtov |
| 2005/0071001 A1 | 3/2005 | Jarvik |
| 2007/0088397 A1 | 4/2007 | Jacobson |
| 2008/0281146 A1 | 11/2008 | Morello |
| 2010/0241223 A1 | 9/2010 | Lee et al. |
| 2011/0178361 A1 | 7/2011 | Yomtov |
| 2011/0270331 A1 | 11/2011 | Peters et al. |
| 2012/0253207 A1 | 10/2012 | Sarkar et al. |
| 2012/0271367 A1 | 10/2012 | Qu et al. |
| 2013/0072846 A1 | 3/2013 | Heide et al. |
| 2014/0012067 A1 | 1/2014 | Poirier |
| 2014/0046120 A1 | 2/2014 | Choi et al. |
| 2014/0058190 A1 | 2/2014 | Gohean et al. |
| 2014/0188148 A1 | 7/2014 | Le Blanc et al. |
| 2015/0057488 A1 | 2/2015 | Yomtov |
| 2015/0073203 A1 | 3/2015 | Wariar et al. |
| 2015/0148587 A1 | 5/2015 | Bourque |
| 2015/0151032 A1 | 6/2015 | Voskoboynikov et al. |
| 2015/0174307 A1 | 6/2015 | Eckman et al. |
| 2015/0290374 A1 | 10/2015 | Bourque et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0228628 A1 | 8/2016 | Medvedev et al. |
| 2016/0263299 A1 | 9/2016 | Xu et al. |
| 2017/0021070 A1 | 1/2017 | Petersen |
| 2017/0080138 A1 | 3/2017 | Yomtov |
| 2018/0050348 A1 | 2/2018 | Whitney |
| 2018/0078689 A1 | 3/2018 | Yomtov |
| 2018/0140760 A1 | 5/2018 | Cotter |
| 2018/0280600 A1 | 10/2018 | Harjes et al. |
| 2018/0280601 A1 | 10/2018 | Harjes et al. |

FOREIGN PATENT DOCUMENTS

| | | |
|---|---|---|
| WO | 2007089500 A2 | 8/2007 |
| WO | 2011123789 A1 | 10/2011 |
| WO | 2016001284 A2 | 1/2016 |
| WO | 2016137743 A1 | 9/2016 |
| WO | 2017117215 A1 | 6/2017 |
| WO | 2017117185 A1 | 7/2017 |
| WO | 2017139113 A1 | 8/2017 |

OTHER PUBLICATIONS

Brisco et al., "The Incidence, Risk, and Consequences of Atrial Arrhythmias in Patients With Continuous-flow Left Ventricular Assist Devices", J Card Surg, vol. 29, Issue 4, 2014, pp. 572-580.
Clark et al., "Hemodynamic Effects of an Irregular Sequence of Ventricular Cycle Lengths During Atrial Fibrillation", Journal of the American College of Cardiology, vol. 30, Issue 4, 2007, pp. 1039-1045.
Enriquez et al., "Clinical Impact of Atrial Fibrillation in Patients With the Heartmate Ii Left Ventricular Assist Device", Journal of the American College of Cardiology, vol. 64, Issue 18, 2014, pp. 1883-1890.
Hayward et al., "Effect of Alteration in Pump Speed on Pump Output and Left Ventricular Filling With Continuous-flow Left Ventricular Assist Device", ASAIO Journal. vol. 57, issue 6, 2011, pp. 495-500.
Maeda et al., "Predictive Control by Physical Activity Rate of a Total Artificial Heart During Exercise", Transactions of the American Society of Artificial Internal Organs, vol. 34, 1988, pp. 480-484.
Maury et al., "First Experience of Percutaneous Radio-frequency Ablation for Atrial Flutter and Atrial Fibrillation in a Patient With Heartmate Ii Left Ventricular Assist Device", Journal of Interventional Cardiac Electrophysiology, vol. 29, Issue 1, 2010, pp. 63-67.
Oswald et al., "Implantable Defibrillator Therapy for Ventricular Tachyarrhythmia in Left Ventricular Assist Device Patients", Eur J Heart Fail., vol. 12, Issue 6, 2010, pp. 593-599.
Oz et al., "Malignant Ventricular Arrhythmias Are Well Tolerated in Patients Receiving Long-term Left Ventricular Assist Devices", Journal of the American College of Cardiology, vol. 24, Issue 7, 1994, pp. 1688-1691.
Raasch et al., "Epidemiology, Management, and Outcomes of Sustained Ventricular Arrhythmias After Continuous-flow Left Ventricular Assist Device Implantation", Am Heart J., vol. 164, Issue 3, 2012, pp. 373-378.

(56) References Cited

OTHER PUBLICATIONS

Ziv et al., "Effects of Left Ventricular Assist Device Therapy on Ventricular Arrhythmias", Journal of the American College of Cardiology, vol. 45, Issue 9, 2005, pp. 1428-1434.

COMMUNICATION METHODS AND ARCHITECTURE FOR HEART TREATMENT SYSTEMS

CROSS-REFERENCE TO RELATED APPLICATIONS

The present application claims the benefit of U.S. Provisional Application No. 62/478,452, filed Mar. 29, 2017, the entire contents of which are hereby incorporated by reference herein in its entirety for all purposes.

The present application is related to U.S. Provisional Application No. 62/478,424, filed Mar. 29, 2017, and concurrently filed U.S. Non-Provisional application Ser. No. 15/939,033, entitled "ADJUSTING PUMP PROTOCOL BASED ON IRREGULAR HEART RHYTHM"; each of which is assigned to the same assignee as the present application and incorporated by reference herein in its entirety for all purposes.

BACKGROUND

The present invention generally relates to heart failure and disease state management systems, and in various respects, methods and systems for communicating information between an implantable blood pump and another device like a cardiac rhythm management device.

Cardiovascular disease remains the leading cause of death globally. Nearly one third of deaths in the U.S. are caused by heart disease, stroke, and other cardiovascular diseases according to the American Heart Association. Nearly one in ten deaths have cardiovascular disease as a contributing factor. Because of the size of this epidemic—nearly 6 million adults in the United States live with heart failure—there remains a need for improving the early diagnosis and treatment of cardiovascular disease. Many people unknowingly live with heart disease until they experience a significant event.

More recently, Ventricular Assist Devices (VADs) have become increasingly common for treating advanced heart failure. Advanced heart failure patients usually refers to patients in New York Heart Association (NYHA) Class III or IV. VAD therapy patients often have several comorbidities such as renal failure, respiratory failure, and other cardiovascular diseases. VAD patients often have other heart failure devices including implanted pacemakers (IPM), implantable cardioverter defibrillators (ICD), cardiac resynchronization therapy (CRT) devices, monitoring systems (e.g., CardioMEMS, implantable cardiac monitors, etc.), and/or other heart failure management devices. While VADs and implantable cardiac rhythm management devices separately provide beneficial heart assist functions, it may be advantageous to communicate information between the implanted devices to diagnose disease, improve therapy through device coordination, and more. And because these systems are not designed to interoperate at present, there is a need for systems and methods to establish communication and interoperability.

There is a need for improved systems for diagnosing and treating heart disease. There is a need for systems and methods for coordinating one or more heart assist devices.

SUMMARY

The present invention generally relates to heart assist systems and therapy. In some aspects, an implantable blood pump is provided. In some aspects, an implantable CRM/ICD or CRT device is provided. In still further aspects of the present invention, a heart assist system is provided that includes an implantable blood pump and an implantable cardiac rhythm management device in coordination with each other. Moreover, other aspects are generally related to methods of communication between two or more heart assist devices.

Communicating information between an implantable blood pump and an implantable cardiac rhythm management device can be beneficial. At first glance, such a goal may seem simple and straightforward, however such coordination between implanted devices comes with a variety of challenges. For instance, Medical Implant Communications Services (MICS) band radio transceivers, which are generally found in CRTs, IPMs and ICDs, may require high power demands for communicating information to the VAD. Such a communications scheme in turn may drastically reduce battery life of a pacemaker by several months to years and, thereby require more frequent and invasive replacement procedures. Similarly, such a communication scheme may require more frequent battery recharging of VAD systems, thereby requiring the patient to be tethered to a power source more frequently and inconveniencing the patient. As such, it may be advantageous to limit the power requirements for the communication scheme between the implanted devices because of the limited power source available to these implants. Accordingly, aspects of the present invention address one or more such challenges.

In some embodiments, a method of assisting a heart of a patient is provided. The method may include sensing a series of electrical pulses from an implantable cardiac rhythm management device electrically pacing the heart of the patient at a first frequency with electrical pulses with a first duration and first voltage. In various embodiments, the sensing can be performed using an implantable blood pump coupled to a heart of a patient. In various embodiments, a sensor is provided for performing the electrical pulse sensing, and the sensor outputs related information to the blood pump. The series of electrical pulses from the implantable cardiac rhythm management device sensed by the implantable blood pump may be associated with a type of abnormal heart rhythm detected by the implantable cardiac rhythm management device. Accordingly, in some embodiments, the implantable cardiac rhythm management device may be configured to sense the heart's electrical activity to determine when the heart is experiencing an abnormal heart rhythm. Additionally, the implantable cardiac rhythm management device may be configured to encode the detected information into the series of electrical pulses sent to the implantable blood pump to specifically identify a type of abnormal heart rhythm detected. For example, the series of electrical pulses may be provided at a second frequency different than the first frequency or may include electrical pulses with a second duration or second voltage different than the first duration or first voltage. The method may further include determining, with the implantable blood pump, the type of abnormal heart rhythm detected by the implantable cardiac rhythm management device by analyzing a frequency of the series of electrical pulses, durations of each of the electrical pulses of the series of electrical pulses, or voltages of each of the electrical pulses of the series of electrical pulses. Thereafter, a pumping protocol of the implantable blood pump may be adjusted based on the type of abnormal heart rhythm determined by the analysis.

In some embodiments, the implantable blood pump determines the type of abnormal heart rhythm by analyzing the frequency of the series of electrical pulses. In some embodiments, the implantable blood pump determines the type of abnormal heart rhythm by referencing a database associating frequencies of sensed electrical pulses with types of abnormal heart rhythm and matches at type of abnormal heart rhythm with the received series of electrical pulses. In some embodiments, the implantable blood pump determines the type of abnormal heart rhythm by comparing the frequency of the series of electrical pulses to one or more frequency thresholds.

Optionally, the implantable blood pump determines the type of abnormal heart rhythm by analyzing durations of each of the electrical pulses of the series of electrical pulses. The series of electrical pulses may comprise a first pulse with a first duration and a second pulse with a second duration that is different than the first pulse.

In some embodiments, the type of abnormal heart rhythm is determined to be a fibrillation of the heart and the pumping protocol may be adjusted to cease the pumping of the implantable blood pump for a predetermined duration of time.

In some embodiments, a heart assist system may be provided. The system may include an implantable blood pump configured to couple with a circulatory system of a patient and to pump blood therethrough. The implantable blood pump may include a pump processor configured to sense a series of electrical pulses from an implantable cardiac rhythm management device electrically pacing the heart of the patient at a first frequency with electrical pulses with a first duration and a first voltage. The series of electrical pulses from the implantable cardiac rhythm management device configured to be sensed by the pump processor may be associated with a type of abnormal heart rhythm detected by the implantable cardiac rhythm management device and may be at a second frequency different than the first frequency or including electrical pulses with a second duration different than the first duration or a second voltage different than the first voltage. The pump processor may be configured to determine the type of abnormal heart rhythm detected by the implantable cardiac rhythm management device by analyzing a frequency of the series of electrical pulses, durations of each of the electrical pulses of the series of electrical pulses or voltages of each of the electrical pulses of the series of electrical pulses. The pump processor can be configured to adjust a pumping protocol of the implantable blood pump based on the type of abnormal heart rhythm determined by the analysis.

In some embodiments, the pump processor is configured to determine the type of abnormal heart rhythm by analyzing the frequency of the series of electrical pulses. In some embodiments, the pump processor is configured to determine the type of abnormal heart rhythm by referencing a database associating frequencies of sensed electrical pulses with types of abnormal heart rhythm. Optionally, the pump processor determines the type of abnormal heart rhythm by comparing the frequency of the series of electrical pulses to one or more frequency thresholds.

In some embodiments, the pump processor determines the type of abnormal heart rhythm by analyzing durations of each of the electrical pulses of the series of electrical pulses. The series of electrical pulses may include a first pulse with a first duration and a second pulse with a second duration that is different than the first pulse.

In some embodiments, when the type of abnormal heart rhythm is determined to be a fibrillation of the heart, the pumping processor adjusts the pumping protocol to cease the pumping of the implantable blood pump for a predetermined duration of time.

Optionally, the electrical pulses of the series of electrical pulses comprise square wave signals.

In still further embodiments, a method of assisting a heart of a patient. The method may include receiving, through a first lead having a first end coupled with an implantable cardiac rhythm management device and a second end opposite the first end coupled with a pump processor of an implantable blood pump, an electrical pace signal from the implantable cardiac rhythm management device. The implantable cardiac rhythm management device may be configured to deliver the electrical pace signal to pump processor of the implantable blood pump with each heart stimulation pulse delivered to the heart of the patient by the implantable cardiac rhythm management device. A pumping of the implantable blood pump may be adjusted based on the received electrical pace signal with the pump processor.

The electrical pace signal may be a square wave signal with a frequency equal to a heart rate of the patient.

The pump processor may be configured to compare a frequency of the electrical pace signal with a first frequency threshold and a second frequency threshold that is greater than the first frequency threshold.

Optionally, the pump processor may adjust the pumping of the implantable blood pump to a first speed when the frequency of the electrical pace signal is below the first frequency threshold, a second speed when the frequency of the electrical pace signal is above the first frequency threshold and below the second frequency threshold, and a third speed when the frequency of the electrical pace signal is above the first frequency threshold and the second frequency threshold. The first speed may be less than the second speed and the second speed may be less than the third speed.

The method may also include detecting, with the implantable cardiac rhythm management device, an abnormal heart rhythm of the heart of the patient, and delivering, with the implantable cardiac rhythm management device, a unique series of electrical pulses through the first lead to the pump processor of the implantable blood pump. Thereafter, the method may include differentiating, with the pump processor, the unique series of electrical pulses from the electrical pace signal which the implantable cardiac rhythm management device delivers simultaneously with the heart stimulation pulses. The received unique series of pulses may then be associated with a pumping protocol and the pumping protocol may be implemented in response to receiving the unique series of pulses.

In some embodiments, the pump processor differentiates the unique series of electrical pulses from the electrical pace signal based on a duration of the electrical pulses of the unique series of electrical pulses.

In some embodiments, the pump processor differentiates the unique series of electrical pulses from the electrical pace signal based on a frequency of the unique series of electrical pulses.

In some embodiments, the pump processor compares the frequency of the unique series of electrical pulses to a threshold frequency to differentiate the unique series of electrical pulses from the electrical pace signal.

In some embodiments, electrical pulses of the unique series of electrical pulses comprise a combination of a first pulse with a first duration and second pulse with a second duration different that the first pulse.

In some embodiments, the pump protocol may be a cessation of pumping for a predetermined duration of time.

In further aspects, a heart assist system may be provided that includes an implantable blood pump configured to couple with a circulatory system of a patient and to pump blood therethrough. The implantable blood pump may include a pump processor, the pump processor including an input. An implantable cardiac rhythm management device may be provided that is configured to deliver heart stimulation pulses to a heart of the patient. A first lead having a first end and a second end opposite the first end may be provided. The first end of the first lead may couple with the implantable cardiac rhythm management device and the second end of the first lead may couple with the input of the pump processor.

The implantable cardiac rhythm management (CRM) device may be configured to deliver an electrical pace signal through the first lead to the implantable blood pump with each heart stimulation pulse delivered to the heart of the patient. In various embodiments, a sensor system is provided for sensing the pulses from the CRM device. In various embodiments, a detector is provided in the VAD for receiving the signals from the CRM device. A converter in the VAD may be provided to convert the signals in the frequency and/or time domain. A converter may be provided to convert the signals between AC and/or DC.

The pump processor of the implantable blood pump may be configured to receive the electrical pace signal from the implantable cardiac rhythm management device and to adjust a pumping of the implantable blood pump based on the received electrical pace signal.

In some embodiments, the electrical pace signal comprises a square wave signal with a frequency equal to a heart rate of the patient.

In some embodiments, the pump processor of the implantable blood pump is configured to compare a frequency of the electrical pace signal with a first frequency threshold and a second frequency threshold that is greater than the first frequency threshold. For example, the processor of the implantable blood pump may adjust the pumping of the implantable blood pump to a first speed when the frequency of the electrical pace signal is below the first frequency threshold, a second speed when the frequency of the electrical pace signal is above the first frequency threshold and below the second frequency threshold, and a third speed when the frequency of the electrical pace signal is above the first frequency threshold and the second frequency threshold. The first speed may be less than the second speed and the second speed may be less than the third speed.

In some embodiments, the implantable cardiac rhythm management device comprises a pacemaker. Optionally, the pacemaker comprises one or more second leads, a header, and internal circuitry for coordinating pacing the heart of the patient with the one or more second leads. The one or more second leads may couple to the internal circuitry through the header of the pacemaker. The first lead may couple the internal circuitry of the pacemaker to the input of the pump processor of the implantable blood pump through the header of the pacemaker. In some embodiments, the one or more second leads and the first lead have the same configuration.

In some embodiments, the implantable cardiac rhythm management device is configured to detect an abnormal heart rhythm of the heart of the patient. The implantable cardiac rhythm management device may also be configured to deliver a unique series of electrical pulses through the first lead to the pump processor of the implantable blood pump. The pump processor may differentiate the unique series of electrical pulses from the electrical pace signal which the implantable cardiac rhythm management device delivers simultaneously with the heart stimulation pulses and may associate the received unique series of pulses with a pumping protocol. Thereafter, the processor may implement the pumping protocol in response to receiving the unique series of pulses.

In some embodiments, the pump processor differentiates the unique series of electrical pulses from the electrical pace signal based on a duration or a voltage of the electrical pulses of the unique series of electrical pulses.

In some embodiments, the pump processor differentiates the unique series of electrical pulses from the electrical pace signal based on a frequency of the unique series of electrical pulses. For example, the pump processor may be configured to compare the frequency of the unique series of electrical pulses to a threshold frequency to differentiate the unique series of electrical pulses from the electrical pace signal.

Optionally, electrical pulses of the unique series of electrical pulses comprise a combination of a first pulse with a first duration and a second pulse with a second duration different from the first pulse.

Various aspects of the invention are directed to a method of detecting heart failure comprising using the system(s) described above.

Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The invention will be better understood upon reading the following description and examining the figures which accompany it. These figures are provided by way of illustration only and are in no way limiting on the invention.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

The present invention generally relates to heart assist systems and in particular methods and systems for communicating information between an implantable blood pump and an implantable cardiac rhythm management device.

Figure 1:
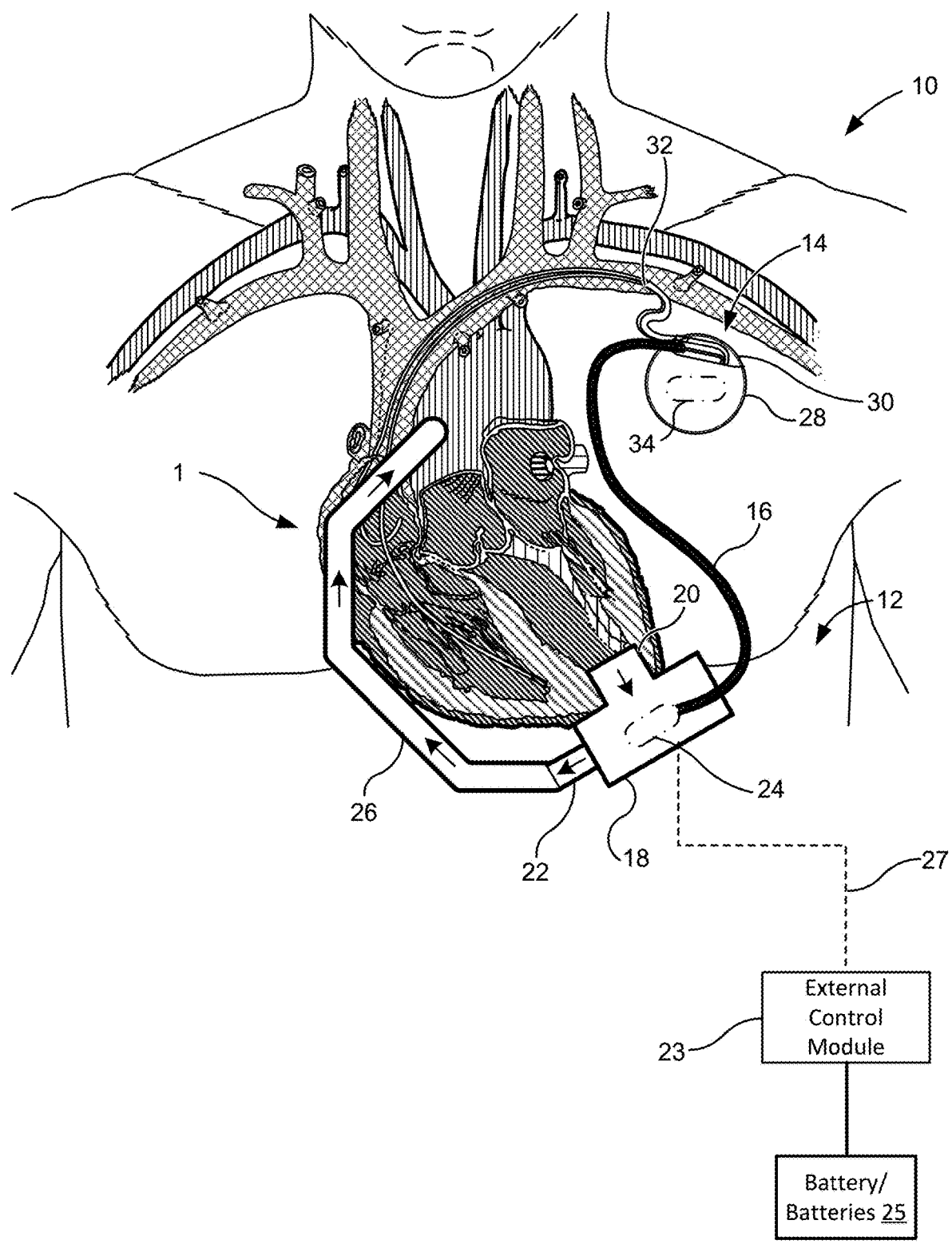
FIG. 1 illustrates an exemplary system of the present invention.

FIG. 1 illustrates an exemplary heart treatment or support system 10 of the present invention. As used herein, "heart treatment system," "heart support system," and "cardiovascular system" are used somewhat interchangeably. Heart treatment system 10 includes an implantable blood pump 12 and an implantable cardiac rhythm management device 14. In various embodiments, the blood pump refers to a ventricular assist system including a pump, battery, and peripherals. In various respects, "heart treatment system" can be used to refer to one or more cardiovascular systems. In one example, heart treatment system refers to a combined system including two subsystems: a left ventricular assist system and a cardiac rhythm management system. In some embodiments, the implantable blood pump 12 and the implantable cardiac rhythm management device 14 may be operatively coupled to one another by a communication line 16 to share information between the implanted devices. In some embodiments, the implantable cardiac rhythm management device 14 may send information to the implantable blood pump 12 through the communication line 16. In other embodiments the implantable blood pump 12 may send information to the implantable cardiac rhythm management device 14 through the communication line 16. And in further aspects, information may be passed from the implantable cardiac rhythm management device 14 to the implantable blood pump 12 and vice-versa.

The blood pump 12 may be configured to couple with the circulatory system (e.g., heart 1) of the patient and to assist in pumping blood therethrough. In some embodiments, the pump 12 includes a pump housing 18 and an inlet cannula 20 and an outlet 22 extending from the housing 18. In some embodiments, the pump 12 may further include an external control module 23. In some embodiments, the pump can be configured similar to an LVAD described in U.S. Patent Publication 2015/0290374; U.S. Patent Publication 2014/0188148; U.S. Pat. Nos. 9,091,271; 8,794,989, 8,682,431; and/or 8,894,561, the contents of which are incorporated herein by reference in their entirety.

The housing 18 may house a rotor of the blood pump 12 an may also include on-board electronics 24 (e.g., processor, battery, sensors, etc.). The inlet cannula 20 may be configured to couple with a chamber of the heart 1 and the rotor of blood pump 12 may draw blood from a coupled heart chamber and output blood through output 22. The output 22 of the pump 12 may couple with a vascular graft assembly 26 which may be coupled with another portion of the patient's circulatory system (e.g., aorta, or the like) to deliver the pumped blood back into the circulatory system of the patient.

In some embodiments, an external control module 23 may be provided to send commands to and receive data from on-board electronics 24 of pump 12. The external control module 23 may be coupled with the pump by a percutaneous cable 27. In some embodiments, one or more batteries 25 may be coupled with the external control module 23 to power the control module 23. The batteries 25 may be external batteries or internal batteries 25.

While pump 12 is generally illustrated as a centrifugal pump, it should be understood that the communications systems and methods described herein are not limited to centrifugal pumps, but are equally applicable to other pump designs (e.g., axial flow or mixed flow, etc.). Additionally, while pump 12 is illustrated as supporting the left ventricle, it should be understood that the pump 12 may be coupled with other portions of the heart 1, such as the right ventricle or other chambers of the heart 1, or other catheter or intravascular pump systems that couple to cardiovascular locations (e.g., descending aorta and other intravascular placements).

The implantable cardiac rhythm management device 14 may be configured to couple with one or more portions of the heart 1 of the patient to pace, resynchronize, and/or sense electrical activity of the heart 1. In some embodiments, the device 14 can be configured similar to a devices described in U.S. Pat. Nos. 8,180,448; 8,295,939; 8,543,205; 7,945,333; 8,295,939; 7,853,325; 8,145,324; 8,180,448; 8,224,462; 8,364,283; 8,712,544; 8,897,887; 7,245,117; 7,439,723; 7,498,799; 7,550,978; 7,679,355; 7,839,153; 6,111,520; and/or 6,278,379, the contents of which are incorporated herein by reference in their entirety. In some embodiments, the implantable cardiac rhythm management device 14 may include a housing 28, a header 30, and one or more leads 32.

The housing 28 may house on-board electronics 34 of the implantable cardiac rhythm management device 14 (e.g., processor, sensor(s), battery, etc.). The header 30 may provide an interface between the electronics 34 and the one or more leads 32 extending from the housing 28.

The one or more leads 32 may operably couple the implantable cardiac rhythm management device 14 to the heart 1 of the patient for pacing, resynchronizing, and/or sensing electrical activity of the heart 1. The one or more leads 32 may couple the implantable cardiac rhythm management device 14 to the right ventricle, right atrium, left ventricle, and/or the left atrium depending on the type of implantable cardiac rhythm management device 14 and treatment needed.

In some embodiments, the implantable cardiac rhythm management device 14 may be a pacemaker, CRT, ICD, or the like. Additionally, while generally illustrated as coupling, e.g., via leads, with the endocardium, the implantable cardiac rhythm management device 14 may be configured to couple with portions of the epicardium to carry out its functions.

Communication line 16 may couple the implantable blood pump 12 with the implantable cardiac rhythm management device 14 so that information may be shared from one implant to the other. For example, the communication line 16 may have a first end that couples to the on-board electronics 34 of the implantable cardiac rhythm management device 14 and a second end that couples to the on-board electronics 24 of the implantable blood pump 12. In some embodiments, the first end connects to the on-board electronics 34 of the implantable cardiac rhythm management device 14 through an open through-hole or plug in the header of the implantable cardiac rhythm management device 14. In some embodiments, the communication line 16 provides an electrical connection between the implantable blood pump 12 and the implantable cardiac rhythm management device 14. Optionally, the communication line 16 may be a lead that may be similar in configuration to the one or more leads 32. As such, the communication line 16 may couple to the on-board electronics 34 of the implantable cardiac rhythm management device 14 through the header 30.

In certain embodiments, the communication line 16 may provide an optical connection between the implantable blood pump 12 and the implantable cardiac rhythm management device 14. An optical connection may be desirable in some situations because the optical cable may be more resistant to corrosion and infection during long term implantation of the implant 14 and may be faster and higher resolution signaling, compared to an implant using an electrical connection. However, an electrical connection may be beneficial in some situations as fewer modifications are required to existing implantable cardiac rhythm management devices.

Figure 2:
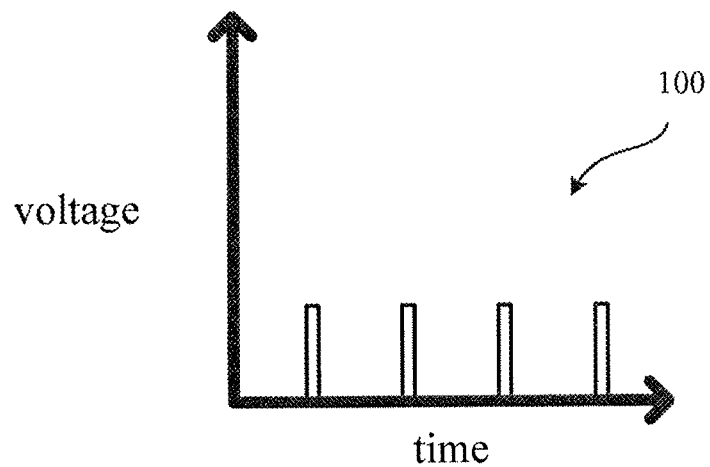
FIG. 2 illustrates an exemplary train of heart stimulation pulses according to some embodiments.

As set forth above, the heart treatment system 10 may improve patient treatment due to the fact that information may be shared between the implanted devices 12, 14. In some embodiments, the implantable cardiac rhythm management device 14 may be configured to deliver heart stimulation pulses to the heart 1 of the patient to pace the patient's heart 1. FIG. 2 illustrates an exemplary train of heart stimulation pulses 100 according to some embodiments. In some embodiments, the heart stimulation pulses 100 may comprise a series of square wave signals.

In some embodiments, the train of heart stimulation pulses 100 delivered are pre-programmed at constant frequency. Optionally, the implantable cardiac rhythm management device 14 may adjust the frequency of the train of heart stimulation pulses 100 based on the patient's needs. For example, in some embodiments, the on-board electronics 34 of the implantable cardiac rhythm management device 14 may include a sensor (e.g., activity sensor, accelerometer, timers) for estimating physical exertion by the patient and/or the time of day. The frequency of heart stimulation pulses 100 may be increased during higher activity (e.g., walking) and/or day time and lowered during lower activity (e.g., sleeping or resting) and/or night time.

In some embodiments, in addition to delivering heart stimulation pulses 100 to the heart 1 of the patient, the implantable cardiac rhythm management device 14 may also be configured to deliver an electrical pace signal through the communication line 16 to the implantable blood pump 12 with each heart stimulation pulse delivered to the heart 1. In at least some embodiments, the electrical pace signal delivered to the implantable blood pump 12 is similar or identical to the heart stimulation pulses 100 delivered to the heart 1 of the patient in frequency, voltage, and/or duration. This may be advantageous in reducing the power requirements for communication information between the implanted devices.

The pump processor of the implantable blood pump 12 may be configured to receive the electrical pace signal from the implantable cardiac rhythm management device 14 and may adjust a pumping of the implantable blood pump 12 based on the received electrical pace signal. In embodiments where the implantable cardiac rhythm management device 14 is configured to adjust the frequency of the train of heart stimulation pulses 100 based on the patient's needs, so too will the frequency of the electrical pace signal delivered to the pump 12. In response, an implantable blood pump 12 may provide additional pumping when the frequency of the electrical pace signal increases to further assist the patient's heart in pumping blood. Similarly, the implantable blood pump 12 may decrease pumping when the frequency of the electrical pace signal decreases, indicating a lower heart rate and a decreased need for blood circulation. Such adjustments in blood pumping may be advantageous in reducing adverse events in pumping action (e.g., suction events or the like). As such, the implantable blood pump may leverage one or more activity sensors of the implantable cardiac rhythm management device to adjust pumping. The one or more activity sensors may comprise electrical pulse detection (e.g., heart rate sensing), one or more accelerometers, time stamp information for time of day information, etc. Thus, the implantable cardiac rhythm management device may be configured to detect patient activity or position (e.g., sitting, standing, laying, walking, running, etc.) or infer activity (e.g., using an internal clock to determine time of day or the like) and may adjust a pacing signal delivered to the heart and/or the pump.

In some embodiments, the implantable cardiac rhythm management device 14 may continuously adjust frequency of the heart stimulation pulses 100 and the electrical pace signal or may switch between one or more pre-programmed modes (e.g., high activity, low activity, resting, sleeping, etc.) to adjust for patient needs throughout the day. Similarly, the implantable blood pump 12 may also continuously adjust pumping of blood in response to changes in frequency of the received electrical pace signal or may switch between one or more pre-programmed pumping modes. For example, the pump processor may be configured to compare a frequency of the electrical pace signal with one or more frequency thresholds. In some embodiments, a first frequency threshold and a second frequency threshold that is greater than the first frequency threshold may be provided. The pump processor may adjust the pumping of the implantable blood pump 12 to a first speed when the frequency of the electrical pace signal is below the first frequency threshold, a second speed when the frequency of the electrical pace signal is above the first frequency threshold and below the second frequency threshold, and a third speed when the frequency of the electrical pace signal is above the first frequency threshold and the second frequency threshold. The first speed may be less than the second speed and the second speed may be less than the third speed.

While the example above is described using two separate thresholds and three separate speeds or pumping modes, it should be understood that one or more frequency thresholds and two or more speeds and/or pumping modes may be utilized in other embodiments.

In some embodiments, the implantable cardiac rhythm management device 14 may be configured to sense electrical signals from the heart 1 and may detect an abnormal heart rhythm of the patient based on the sensed electrical signals. Optionally, the implantable cardiac rhythm management device 14 may deliver a unique series of electrical pulses through the communication line 16 to the pump processor of the implantable blood pump 12. The unique series of electrical pulses may be associated with the specific type of abnormal heart rhythm detected by the implantable cardiac rhythm management device 14. In some embodiments, the series of electrical pulses comprise a series of simple square wave signals. This may be advantageous in reducing power requirements of the communications method.

The pump processor may receive the unique series of electrical pulses and may decode the unique series of electrical pulses to determine the type of abnormal heart rhythm being experienced by the patient. In response, the pump processor may be configured to adjust and implement a pumping protocol of the implantable blood pump 12 to account for the abnormal heart rhythm. For example, in some embodiments, the pump processor may temporarily cease operation of the pump in the event that fibrillation of the heart is sensed. After defibrillation, the pump 12 may resume pumping.

In some embodiments, the pump processor may decode the received unique series of electrical pulses using a look-up table. For example, the processor may compare the received series of electrical pulses to a database that stores a plurality of different possible signals and associates each of these possibilities with a type of abnormal heart rhythm. By identifying a match between the received signal and the signal stored in the database, the pump processor may then match the received signal with a specific type of abnormal heart rhythm signaled by the implantable cardiac rhythm management device 14.

Optionally, the pump processor may decode the received unique series of electrical using one or more thresholds. For example, one or more frequency, voltage, and/or duration thresholds may be utilized to decode the received unique series of electrical pulses.

In some embodiments, the implantable cardiac rhythm management device 14 may be configured to deliver heart stimulation pulses 100 to the heart 1 and also configured to sense electrical signals from the heart to detect abnormal heart rhythms. Accordingly, in some embodiments, the implantable cardiac rhythm management device 14 may deliver an electrical pace signal through the communication line 16 to the implantable blood pump 12 with each heart stimulation pulse delivered to the heart 1 and also a unique series of electrical pulses through the communication line 16 to the pump processor of the implantable blood pump 12 when an abnormal heart rhythm is detected. The pump processor may differentiate the unique series of electrical pulses from the electrical pace signal 100 which the implantable cardiac rhythm management device 14 delivers simultaneously with the heart stimulation pulses and may associate the received unique series of pulses with a pumping protocol. Thereafter, the processor may implement the pumping protocol in response to receiving the unique series of pulses while also adjusting pumping for heart rate.

Figure 3:
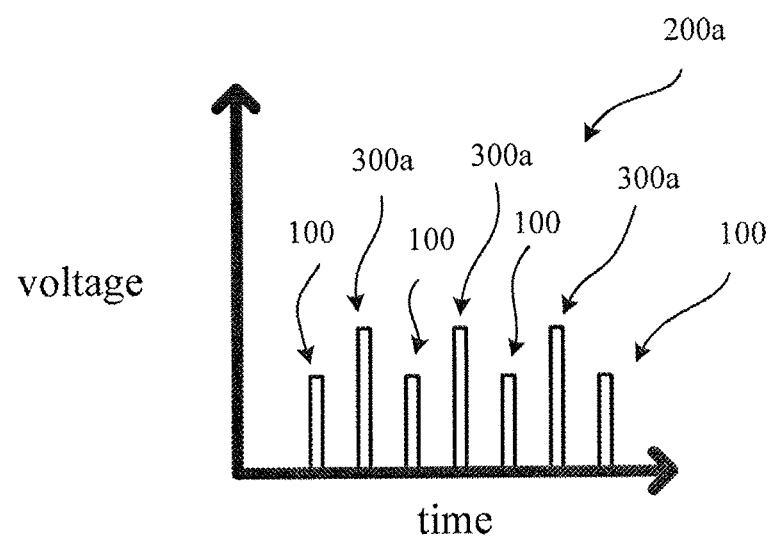
FIG. 3 illustrates an exemplary series of electrical pulses from an implantable cardiac rhythm management device to a blood pump to communication physiological information.

For example, FIGS. 3-6 illustrate a plurality of exemplary electrical pulses 200a-200d from an implantable cardiac rhythm management device 14 to a blood pump 12 to communication physiological information. In FIG. 3, the series of electrical pulses 200a may comprise a series of square wave signals. The series of electrical pulses 200a may include the electrical pace signal 100 that is associated with the heart stimulation pulses delivered to the patient. Additionally, the series of electrical pulses 200a may also include the unique series of electrical pulses 300a associated with a type of abnormal heart rhythm detected by the implantable cardiac rhythm management device 14. As illustrated, in some embodiments, the unique series of electrical pulses 300a may overlap in time with the electrical pace signal 100. In this embodiment, the pump processor may differentiate the series of electrical pulses 300a from the pace signal 100 based on a voltage of the electrical pulses in the series of electrical pulses 200a. For example, the voltage of the pace signal 100 may be higher or lower than the electrical pulses associated with the abnormal heart rhythm. Accordingly, in some embodiments, the pump processor may utilize a voltage threshold to differentiate the series of electrical pulses 300a from the pace signal 100. After differentiating the series of electrical pulses 300a from the pace signal 100, the pump processor may adjust the pump 12 according to one or both of the signals received from the implantable cardiac rhythm management device 14. While the series of electrical pulses 300a is illustrated as including a plurality of higher voltage electrical pulses, it should be understood that a single higher or lower voltage pulse may be delivered to indicate the detection of an abnormal heart rhythm.

Figure 4:
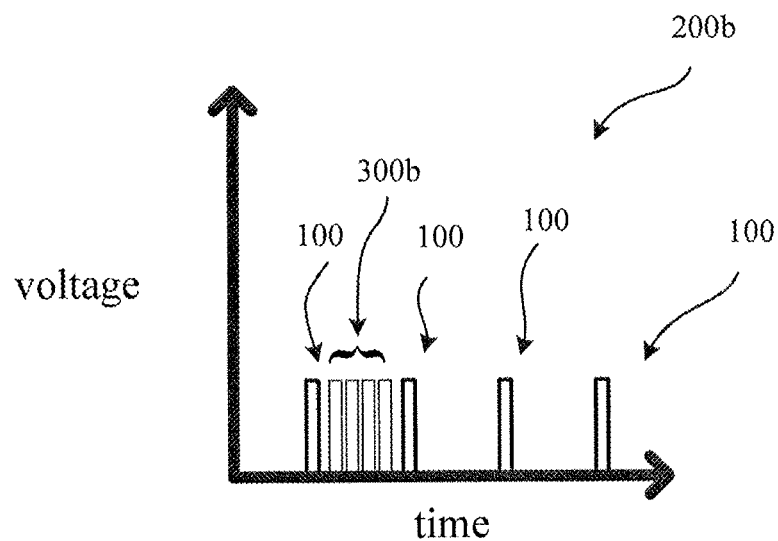
FIG. 4 illustrates another exemplary series of electrical pulses from an implantable cardiac rhythm management device to a blood pump to communication physiological information.

FIG. 4 illustrates another exemplary series of electrical pulses 200b from an implantable cardiac rhythm management device 14 to a blood pump 12 to communication physiological information. The pump 12 may differentiate the series of electrical pulses 300b (associated with the abnormal heart condition) from the pace signal 100 (associated with the heart stimulation signals) based on a frequency of the electrical pulses in the series of electrical pulses 200b. For example, the electrical pulses 300b, associated with the abnormal heart rhythm, may be delivered to the pump 12 at a higher frequency than the pacing signal 100. Accordingly, in some embodiments, the pump processor may utilize a frequency threshold to differentiate the series of electrical pulses 300b from the pace signal 100. For example, given that the pacing signal 100 is associated with a heart rate of the patient, it would be understood that there is an upper limit to this rate. The series of electrical pulses 300b associated with the abnormal heart rhythm may be delivered to the pump 12 at a frequency which exceeds the heart rate upper limit. For example, in some embodiments, the upper limit may be based on a highest expected heart rate for a heart failure patient. For example, the upper limit may be 120 bpm in some instances, 150 bpm, 160 bpm, 200 bpm, or more (e.g., 250 bpm) in other instances. Optionally, the implantable cardiac rhythm management device 14 may be preprogrammed with an maximum heart stimulation rate (e.g., for safety purposes or the like). The series of electrical pulses 300b associated with the abnormal heart rhythm may be delivered to the pump 12 at a frequency which exceeds the preprogrammed maximum heart stimulation rate of the implantable cardiac rhythm management device 14. As such, the pump 12, when receiving electrical pulses that exceed this frequency threshold would automatically recognize that the series of pulses are associated with a type of abnormal heart rhythm and may proceed to decode the type detected. Thereafter, the pump processor may adjust the pump 12 accordingly.

Figure 5:
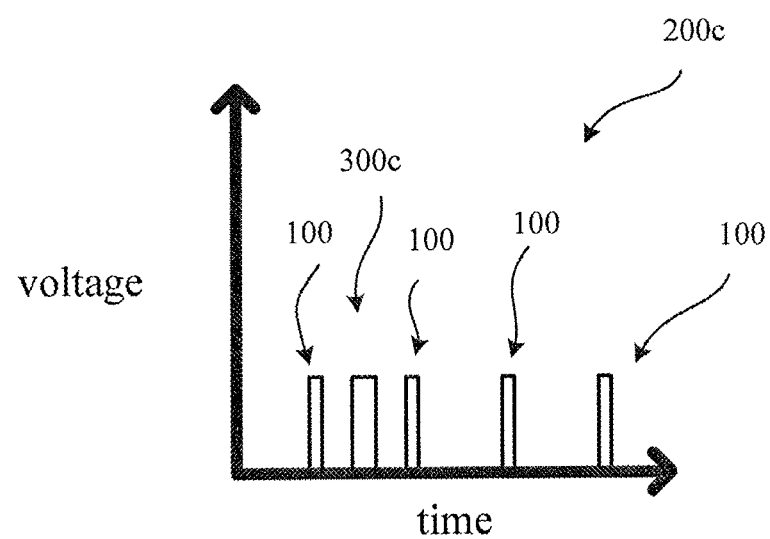
FIG. 5 illustrates another exemplary series of electrical pulses from an implantable cardiac rhythm management device to a blood pump to communication physiological information.

FIG. 5 illustrates another exemplary series of electrical pulses 200c from an implantable cardiac rhythm management device 14 to a blood pump 12 to communication physiological information. In this embodiment, the pump processor may differentiate the electrical pulse 300c (associated with the abnormal heart condition) from the pace signal 100 (associated with the heart stimulation signals) based on a duration of the electrical pulses in the series of electrical pulses 200c. For example, the electrical pulse 300c may have a longer duration than the pulses associated with the pace signal 100. Accordingly, in some embodiments, the pump processor may utilize a pulse duration threshold to differentiate the electrical pulse 300c from the pace signal 100. While only a single electrical pulse 300c is illustrated, it should be understood that one or more electrical pulses 300c may be associated with different types of abnormal heart conditions. Additionally, more complex information may be transmitted to the pump 12 and decoded if electrical pulse 300c is transmitted in varying combinations of long pulses and short pulses, similar to Morse code.

Figure 6:
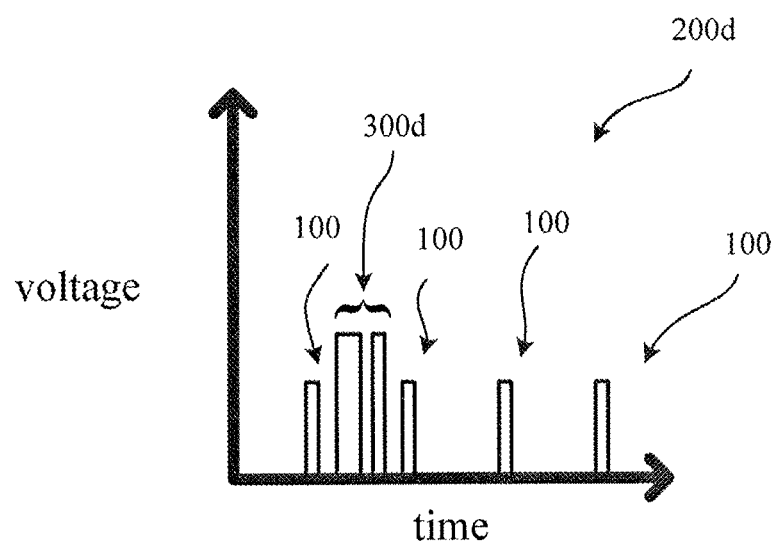
FIG. 6 illustrates another exemplary series of electrical pulses from an implantable cardiac rhythm management device to a blood pump to communication physiological information.

FIG. 6 illustrates another exemplary series of electrical pulses 200d from an implantable cardiac rhythm management device 14 to a blood pump 12 to communication physiological information. The pump processor may differentiate the series of electrical pulses 300d from the pace signal 100 (associated with the heart stimulation signals) based on a duration, voltage and/or frequency of the electrical pulses in the series of electrical pulses 200c. By varying the voltage, duration, and/or frequency of the electrical pulses of the series 300d, the implantable cardiac rhythm management device 14 may be able to deliver more complex information including, but not limited to, the abnormal heart conditions detected by the implantable cardiac rhythm management device 14. Thereafter, the pump processor may adjust and implement the pump protocol, similar to the embodiments described above.

In some embodiments, a unique series of electrical pulses may be indicative of a start/stop to a communication. For example, a first unique series of electrical pulses may be received by the pump 12 which are indicative of a start of communication. A second unique series of electrical pulses may follow the first unique series of electrical pulses which communicate specific information to the pump 12. A third unique series of electrical pulses may be indicative of a stop to communication. The first and third unique series of electrical pulses may be identical or different. The start communication signal may cause the pump processor to "wake up" and start receiving the second series of electrical pulses associated with the information transmitted by the implantable cardiac rhythm management device 14. Similarly the stop communication signal may cause the pump processor standby until the next start communication signal is received.

In some embodiments, the implantable cardiac rhythm management device and the implantable blood pump may be configured to communicate wirelessly. For example in some embodiments, the implantable cardiac rhythm management device may encode information (sensed patient information, time stamps, etc.) and transmit the information by Bluetooth communication to the implantable blood pump. As such, the implantable blood pump may be configured to receive the Bluetooth signal from the implantable cardiac rhythm management device and to decode the signal to determine the type of information sent from the implantable cardiac rhythm management device (e.g., heart rate information, abnormal heart rhythm detection, information associated with patient position or activity, etc.). Thereafter, the implantable blood pump may be configured to adjust a pumping operation (changing pumping modes, speeds, etc.).

In some embodiments, the implantable cardiac rhythm management device and implantable blood pump may communicate through the conductive pathways of the tissue, similar to the communication methods and systems described in U.S. Patent Publication No. 2007/0088397, the contents of which are incorporated herein by reference in their entirety. Accordingly, in some embodiments, the implantable cardiac rhythm management device may communicate by emitting an electric field which may be conducted through the tissue and detected by one or more sensors of the implantable blood pump.

While the above systems are generally described for communication between implanted devices, it should be understood that the cardiac rhythm management device and/or the pump may not be fully implanted in other embodiments.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of assisting a heart of a patient, the method comprising:
receiving, through a first lead having a first end coupled with an implantable cardiac rhythm management device and a second end opposite the first end coupled with a pump processor of an implantable blood pump, an electrical pace signal from the implantable cardiac rhythm management device, the implantable cardiac rhythm management device delivering the electrical pace signal to the pump processor of the implantable blood pump;
adjusting a pumping protocol of the implantable blood pump based on the received electrical pace signal with the pump processor.

2. The method of claim 1, wherein the electrical pace signal is received with each heart stimulation pulse delivered to the heart of the patient by the implantable cardiac rhythm management device.

3. The method of claim 1, wherein the electrical pace signal comprises a square wave signal with a frequency equal to a heart rate of the patient.

4. The method of claim 1, further comprising comparing, with the pump processor of the implantable blood pump, a frequency of the electrical pace signal with a first frequency threshold and a second frequency threshold that is greater than the first frequency threshold.

5. The method of claim 4, further comprising adjusting, with the pump processor of the implantable blood pump, the pumping of the implantable blood pump to a first speed when the frequency of the electrical pace signal is below the first frequency threshold, a second speed when the frequency of the electrical pace signal is above the first frequency threshold and below the second frequency threshold, and a third speed when the frequency of the electrical pace signal is above the first frequency threshold and the second frequency threshold, the first speed being less than the second speed and the second speed being less than the third speed.

6. The method of claim 1, further comprising detecting, with the implantable cardiac rhythm management device, an abnormal heart rhythm of the heart of the patient, and delivering, with the implantable cardiac rhythm management device, a unique series of electrical pulses through the first lead to the pump processor of the implantable blood pump.

7. The method of claim 6, wherein electrical pulses of the unique series of electrical pulses comprise a combination of a first pulse with a first duration and second pulse with a second duration different that the first pulse.

8. The method of claim 6, further comprising differentiating, with the pump processor, the unique series of electrical pulses from the electrical pace signal; associating the received unique series of pulses with a pumping protocol; and implementing the pumping protocol in response to receiving the unique series of pulses.

9. The method of claim 8, wherein the pump protocol comprises a cessation of pumping for a predetermined duration of time.

10. The method of claim 8, wherein the pump processor differentiates the unique series of electrical pulses from the electrical pace signal based on a duration of the electrical pulses of the unique series of electrical pulses.

11. The method of claim 8, wherein the pump processor differentiates the unique series of electrical pulses from the electrical pace signal based on a frequency of the unique series of electrical pulses.

12. The method of claim 11, wherein the pump processor compares the frequency of the unique series of electrical pulses to a threshold frequency to differentiate the unique series of electrical pulses from the electrical pace signal.

13. The method of claim 1, wherein the first lead comprises a communication line that couples the first end to on-board electronics of the implantable cardiac rhythm management device through a header of the implantable cardiac rhythm management device to the pump processor at the second end.

14. A heart treatment system, comprising:
an implantable blood pump configured to couple with a circulatory system of a patient and to pump blood therethrough, the implantable blood pump comprising a pump processor, the pump processor including an input;
an implantable cardiac rhythm management device configured to deliver heart stimulation pulses to a heart of the patient;
a first lead having a first end and a second end opposite the first end, the first end of the first lead coupling with the implantable cardiac rhythm management device and the second end of the first lead coupled with the input of the pump processor;
wherein the implantable cardiac rhythm management device is configured to deliver an electrical pace signal through the first lead to the implantable blood pump; and
wherein the pump processor of the implantable blood pump is configured to receive the electrical pace signal from the implantable cardiac rhythm management device and to adjust a pumping of the implantable blood pump based on the received electrical pace signal.

15. The heart treatment system of claim 14, wherein the implantable cardiac rhythm management device is configured to deliver the electrical pace signal through the first lead to the implantable blood pump with each heart stimulation pulse delivered to the heart of the patient.

16. The heart treatment system of claim 14, wherein the electrical pace signal comprises a square wave signal with a frequency equal to a heart rate of the patient.

17. The heart treatment system of claim 14, wherein the pump processor of the implantable blood pump is configured to compare a frequency of the electrical pace signal with a first frequency threshold and a second frequency threshold that is greater than the first frequency threshold.

18. The heart treatment system of claim 17, wherein the processor of the implantable blood pump adjusts the pumping of the implantable blood pump to a first speed when the frequency of the electrical pace signal is below the first frequency threshold, a second speed when the frequency of the electrical pace signal is above the first frequency threshold and below the second frequency threshold, and a third speed when the frequency of the electrical pace signal is above the first frequency threshold and the second frequency threshold, the first speed being less than the second speed and the second speed being less than the third speed.

19. The heart treatment system of claim 14, wherein the implantable cardiac rhythm management device comprises a pacemaker.

20. The heart treatment system of claim 19, wherein the pacemaker comprises one or more second leads, a header, and internal circuitry for coordinating pacing the heart of the patient with the one or more second leads, and wherein the one or more second leads couple to the internal circuitry through the header of the pacemaker; and wherein the first lead couples the internal circuitry of the pacemaker to the input of the pump processor of the implantable blood pump through the header of the pacemaker.

21. The heart treatment system of claim 20, wherein the one or more second leads and the first lead have the same configuration.

22. The heart treatment system of claim 14, wherein the implantable cardiac rhythm management device is configured to detect an abnormal heart rhythm of the heart of the patient.

23. The heart treatment system of claim 22, wherein the implantable cardiac rhythm management device is configured to deliver a unique series of electrical pulses through the first lead to the pump processor of the implantable blood pump; and wherein the pump processor differentiates the unique series of electrical pulses from the electrical pace signal and associates the received unique series of pulses with a pumping protocol and implements the pumping protocol in response to receiving the unique series of pulses.

24. The heart treatment system of claim 23, wherein electrical pulses of the unique series of electrical pulses comprise a combination of a first pulse with a first duration and a second pulse with a second duration different from the first pulse.

25. The heart treatment system of claim 23, wherein the pump protocol comprises a cessation of pumping for a predetermined duration of time.

26. The heart treatment system of claim 23, wherein the pump processor differentiates the unique series of electrical pulses from the electrical pace signal based on a duration of the electrical pulses of the unique series of electrical pulses.

27. The heart treatment system of claim 23, wherein the pump processor differentiates the unique series of electrical pulses from the electrical pace signal based on a frequency of the unique series of electrical pulses.

28. The heart treatment system of claim 27, wherein the pump processor is configured to compare the frequency of the unique series of electrical pulses to a threshold frequency to differentiate the unique series of electrical pulses from the electrical pace signal.

* * * * *